United States Patent [19]

Smith

[11] Patent Number: 5,063,370

[45] Date of Patent: Nov. 5, 1991

[54] HYPODERMIC SYRINGE NEEDLE DETECTION ALARM

[76] Inventor: Steven C. Smith, 2315 N. Pearl #10-185, Tacoma, Wash. 98406

[21] Appl. No.: 521,678

[22] Filed: May 10, 1990

[51] Int. Cl.$^5$ .................... G08B 21/00; H01H 47/00
[52] U.S. Cl. .................... 340/540; 128/919; 340/321; 361/170
[58] Field of Search ........... 340/540, 541, 550, 321, 340/562, 568, 572; 128/919, 917; 361/170; 200/61.59, 61.19, 61.42

[56] References Cited

U.S. PATENT DOCUMENTS

| | | | |
|---|---|---|---|
| 3,959,789 | 5/1976 | McGahee | 340/568 X |
| 4,843,014 | 6/1989 | Cukier | 128/638 X |
| 4,874,384 | 10/1989 | Nunez | 128/919 X |
| 4,890,094 | 12/1989 | Kopel | 340/568 X |
| 4,890,734 | 1/1990 | Gach | 128/919 X |
| 4,910,803 | 3/1990 | Cukier | 128/918 X |
| 4,915,698 | 4/1990 | Levenson | 128/919 X |
| 4,921,491 | 5/1990 | Champ | 128/919 X |
| 4,938,514 | 7/1990 | D'Addezio | 128/919 X |
| 4,938,745 | 7/1990 | Sagstetter | 128/917 X |
| 4,947,868 | 8/1990 | Schodman | 128/917 X |

*Primary Examiner*—Glen R. Swann, III
*Assistant Examiner*—Thomas J. Mullen, Jr.

[57] ABSTRACT

A hypodermic syringe needle detector consisting of a normally open circuit adapted to be closed when a hypodermic syringe needle penetrates the device and simultaneously makes electrical contact between two or more elctrically conductive surfaces. Closing the circuit energizes a sensory alarm such as an audio signal or light.

20 Claims, 2 Drawing Sheets

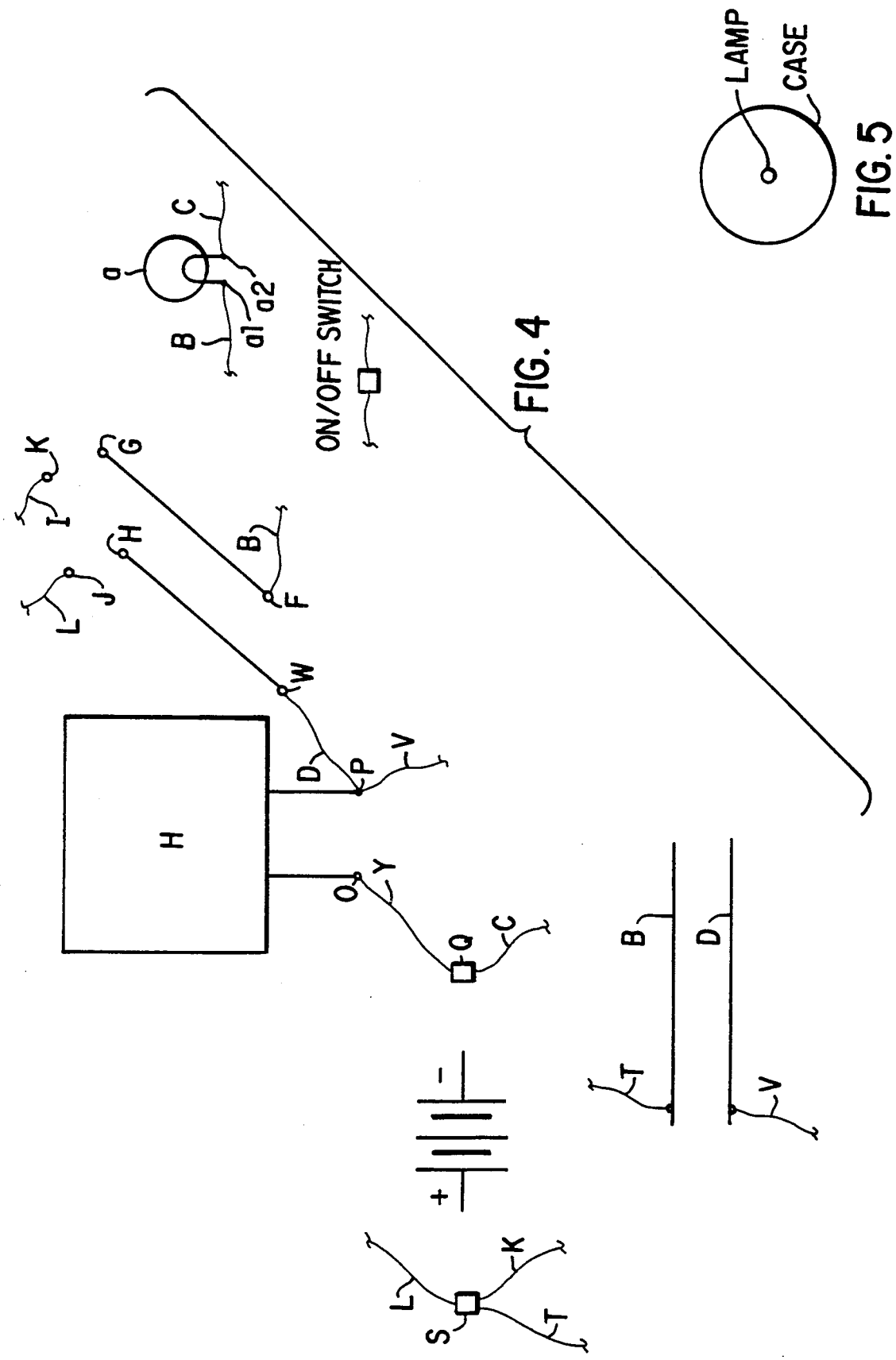

HYPODERMIC SYRINGE NEEDLE DETECTION ALARM

BACKGROUND OF THE INVENTION

1. Field of the Invention

This invention relates in general to warning alarms and in particular to warning alarms which detect the presence of hypodermic syringe needles.

2. Prior Art

Fear of puncture by a contaminated hypodermic syringe needle is common among health care workers, police officers and others who may come into contact with contaminated needles. In the past, protection has relied upon the use of protective clothing. No device is known, however, which can be used by police officers or others to search in pockets or similar areas for needles and which will raise an alarm if a needle is detected. The objective of the present invention is to provide a warning device which will warn of potential exposure to contaminated needles so that appropriate measures may be taken to avoid contamination from needles.

SUMMARY OF THE INVENTION

As stated above the primary objective of the invention is to warn of the presence of needles in areas where visual inspection is difficult. This invention is a device to detect metal needles by using the ability of the metal needle to conduct electricity and complete an electric circuit which will then trigger an alarm.

BRIEF DESCRIPTION OF THE DRAWINGS

FIG. 4 demonstrates in general terms the circuitry of a needle detection device in accordance with the present invention.

FIG. 5 is a top view of a needle detection device in accordance with the present invention.

DETAILED DESCRIPTION

Figure 2:
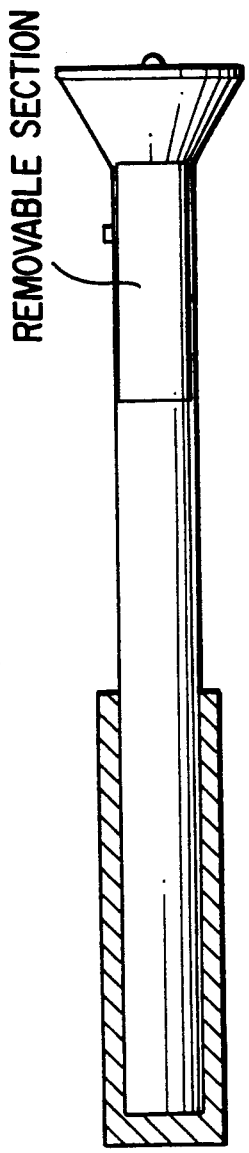
FIG. 2 is a side perspective of the device of FIG. 1.
Figure 1:
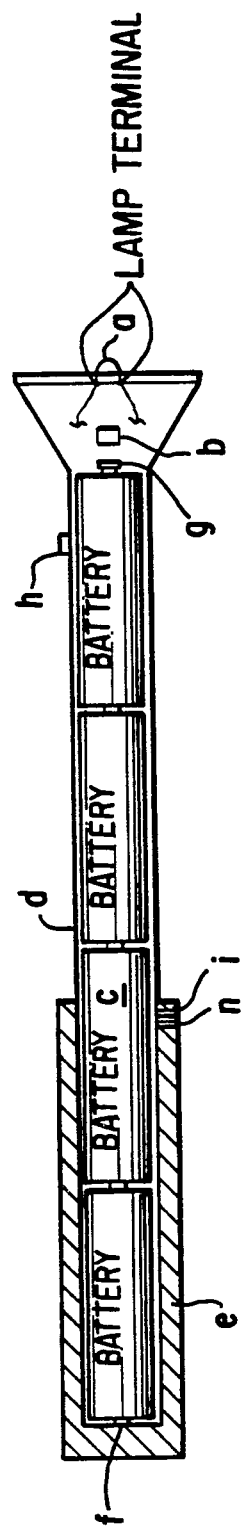
FIG. 1 is a cutaway drawing of a needle detection device in accordance with the present invention.

As shown in the drawings, the preferred hypodermic syringe needle detection alarm device in accordance with the present invention includes a portable case of cylindrical shape which preferably is of strong molded plastic material. The case is hollow so that it can contain the power source and other working parts. At the bottom end of the device attached to the outside of the case is the external detection layer, more particularly described in FIG. 3.

In detail the case $1d$ has at its top a preferably direct current lamp $1a$ and is connected to said lamp at $4a2$ and $4a1$ by preferably metal wire $4b$ & $4c$. Continuing down the case is shown on/off switch $1h$, relay $1b$, power source $1c$, power source terminals $1f$ & $1g$ and external detection circuit $1e$.

The circuitry is more particularly described in FIG. 4. Lamp $4a$ is connected at terminal $4a2$ to preferably wire $4c$ which in turn connects to power source terminal $4q$. Said lamp is also connected at terminal $4a1$ to preferably wire $4b$ which in turn connects to relay terminal $4f$. Terminal $4f$ is connected to terminal $4q$ by moving pole $4fg$. Space $4gi$ represents air space which is evident when the on/off switch $4m$ is in the off position or when the on/off switch is in the on position but there is no electrical connection between the conductive layers shown in FIG. 3 as $3b$ and $3d$ (under normal operating conditions when the power source is fully operable) but terminals $4g$ and $4i$ will be in electrical contact when the electromagnet portion of the relay $4h$ is activated. Preferably wire connection $4k$ extends from relay terminal $4i$ to power source terminal $4s$.

Figure 3:
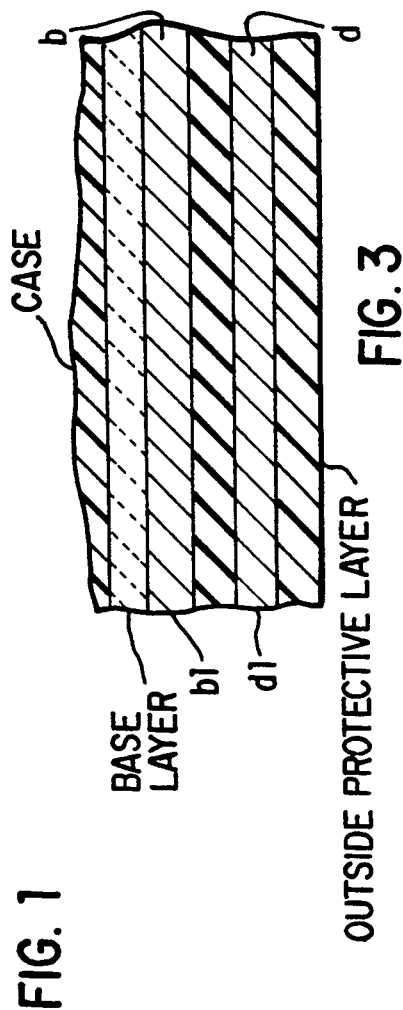
FIG. 3 is an enlarged, fragmentary cross-section of the external detection layer of said device.

Preferably wire $4t$ connects terminal $4s$ to external detection layer $4B$, more precisely said wire connects at a point $3b1$ as indicated in FIG. 3. Preferably wire $4v$ connects at point $3d1$ (layer $4D$) and runs to point $4p$ which is one terminal of the electromagnet portion of the relay. Terminal $4o$ is the other terminal of the electromagnet and connects to power source terminal $4Q$ by preferably wire connection $4y$. Preferably wire connects from point $4p$ to relay terminal $4w$ via said wire $4d$. Terminal $4w$ connects to terminal $4h$ of the relay via moving pole $4wh$. Space $4hj$ represents air space which is evident when the on/off switch is in the off position or when the on/off switch is in the on position but there is no electrical connection between said conductive layers (under normal operating conditions) but under normal operating conditions when the power source is fully operable terminals $4h$ & $4j$ will be in electrical contact when the electromagnet portion of said relay is activated. Preferably wire $41$ connects terminal $4j$ with power source terminal $4s$. Preferably wire connection $4t$ extends from power source terminal $4s$ to detection layer terminal $3b1$ through point $1h$ which is an opening in the case $1d$. Preferably wire connection $4v$ extends from detection layer terminal $3d1$ through point $1i$ which is an opening in the case $1d$.

Inside the case and inserted in a straight line in the preferred version lie four AA size flashlight batteries of approximately 1.5 volts DC each which serve as the power source for the device. In the preferred version all electronic parts operate on six volts DC, said voltage being approximate.

Referring now to FIGS. 1 through 4 which are overall drawings of a preferred embodiment of the invention, the figures represent a portable, handheld, dry cell battery powered device which emits an alarm in the form of light (alternatively sound also) when in normal operation the external detection layers are pierced by an electrically conductive hypodermic syringe needle. A case of molded plastic serves as the container for the working parts and also as a base upon which the external detection layers, which comprise two conductive metal foil layers separated by a non-electrically conductive insulative material, preferably common plastic stretch wrap for the insulator between the two conductive layers and common aluminum foil for the two conductive layers. Attached to the bottom end of the case by preferably common cyanoacrylate adhesive is the base layer, which preferably is of cork in a thin layer, an alternative being rubber in a thin layer, such layer being preferably about 1.5 to 2 millimeters in thickness, covering the bottom preferably 100 approx. millimeters of the cylindrical case. The cylindrical case should preferably be at least about 15 millimeters in inside diameter in order to accommodate the AA batteries(alternatively smaller or larger batteries could be used, with appropriate adjustment in the inside diameter of the case). The total length of the case should preferably be about 300 millimeters and approx. 50 millimeters from the top (the top being where the lamp is located) the outside diameter should flare to about 40 to 50 millimeters so that said portion may serve as a convenient object for a handhold on the device while in use. Regarding the outside diameter of the case below said top portion such outside diameter should not exceed about 20 millimeters so that the device will more easily fit inside pockets. Regarding the second layer which preferably covers about the bottom 100 millimeters (all external detection layers cover about the bottom 100 millimeters of the case) and is attached to the base layer preferably by common cyanoacrylate adhesive, this layer of preferably common aluminum foil would preferably comprise two layers of said foil and would total about 0.1 millimeter in width, preferably these two foil layers which collectively comprise one foil conductive layer of the device should be held in proximity by friction from the immediately above and below layers. Alternatively a greater number of individual metal foil layers could be used to comprise the said conductive layer (or a single foil layer could be used). Surrounding the foil layer lies a non-electrically conducting layer comprising preferably about 2 layers of common plastic stretch wrap forming collectively a single insulative layer between the conductive layer mentioned above and the conductive layer described below in order that no electrical contact occurs between said two conductive layers unless an electrically conductive object pierces the outside conductive layer and continues on to make electrical contact with the inside conductive layer in such a fashion that electrical contact is simultaneously made between both said conductive layers.

An electrical terminal located on the inside conductive layer provides electrical connection with the power source via preferably metal wire as shown in the figures presented. A second electrically conductive layer constructed preferably identically to the above-mentioned conductive layer rests on the insulative layer, with an electrical terminal attached preferably as shown in the figures to provide electrical contact via preferably metal wire with the remainder of the circuitry of the device. The second conductive layer (outside layer) is covered by a flexible porous, about 5 millimeters width flexible material, preferably sponge type plastic, alternatively about four layers of common plastic stretch wrap may be used for this layer which is the outside protective layer of the external detection layers. Preferably all said layers cover about the bottom 100 millimeters of the case in order to provide sufficient contact area for the device to contact hypodermic syringe needles when in use.

In the preferred embodiment, the two terminals at either end of the power source are metal coils which in use will be partially compressed by the batteries when said batteries are in place in order to provide good electrical contact between the power source and said terminals, and suitable terminals will attach to said coils for attachment of all wires as shown in the figures. The preferable version will also have an on/off switch which for simplicity was not included in the FIG. 4 circuit drawings but the preferred version in use will have one terminal at 4s which will connect electrically to metal wire, the other end of said wire being connected to one terminal of the on/off switch (said on/off switch having two terminals) connected to the second terminal of said on/off switch will be a metal wire which will electrically contact the positive pole of the power source at a point between said pole and terminal 4s in such a fashion that electricity does not flow from the positive pole of said power source to point 4s unless said on/off switch is on the "on" position.

In the preferred version the external protective layers will be removable and replaceable when worn. In use, by way of example and not limitation, the bottom portion of the device will be inserted into the pockets of a suspect in police custody who is being searched. The bottom end of the device would be manipulated around the inside of the pocket in such a manner that if an exposed hypodermic syringe needle is in the pocket, said needle will penetrate the outer protective layer, the outside conductive layer, the insulative layer, and then make electrical contact with the inside conductive layer which, by making electrical contact between the two said conductive layers, complete an electrical circuit and trigger the alarm, the relay locking in such a manner that the alarm will continue to emit warning until the on/off switch is turned to the "off" position even if electrical connection is lost between the two said conductive layers. The alarm will alert the searching officer.

Alternatives, by way of example and not limitation, can include a buzzer or other sound device as well as a lamp or light emitting diode for the alarm warning, different power sources or voltages could be used, and different types of conductors or insulators could be used, as well as different materials for the case. Different types of relays could also be used.

While preferred embodiments of the present invention have been shown and described herein, it will be obvious that such embodiments are provided by way of example only. Numerous variations, changes and substitutions will occur to those skilled in the art without departing from the invention herein. Accordingly, it is intended that the invention be limited only by the spirit and scope of the appended claims.

The base layer of the device is preferably an insulator and is bonded to the case, then covered by a second layer of electrically conductive material, which is then covered by an electrically non-conductive material which is sufficiently permeable to permit the passage through it of a hypodermic syringe needle, said layer also being covered by a conductive layer which is also sufficiently permeable to permit the passage through it of a hypodermic syringe needle. This last mentioned layer is also covered by another layer which is sufficiently permeable to permit the passage through it of a hypodermic syringe needle. Said conductive layers are attached to said power source and said electromagnet in the manner shown in the drawings and in such a manner that when there is electrical connection between said two conductive layers said electromagnet is supplied with power and said electromagnet moves the moving poles of said switch in such a manner that said moving poles move to make electrical contact with those terminals which, in the absence of said power to said electromagnet, are separated from said moving poles by airspace. No electrical connection is present between the two conductive layers unless a conductive material such as a needle simultaneously makes electrical contact with both such conductive layers, said space between said two conductive layers being the only point of opening in said detection circuit which includes as part of said circuit said external detection layers, as demonstrated in the drawings.

As shown in the drawings, the detection circuit drives an electromagnet when electrical contact is made with both said conductive layers at the same time. Said electromagnet is connected to said switch in such a manner that when said electromagnet is driven the moving poles make contact with the switch terminals which close the circuits which drive the alarm and which lock the electromagnet into a driven state thus locking the alarm on. In the absence of any initial electrical contact between said conductive layers, the electromagnet will not be driven, however once the electrical contact between said conductive layers is made, the switch, which acts as a relay, will lock the alarm into a warning alert state.

What I claim is:

1. A hypodermic syringe needle detection device comprising two layers of permeable electrically conductive material which is susceptible to puncture by a hypodermic syringe needle separated by permeable electrically non-conductive material which is susceptible to puncture by a hypodermic syringe needle, a means to provide electrical connection from one pole of a two pole direct current power source to pole one of a two pole alarm; a means to provide electrical connection from pole two of said two pole alarm to the second layer of said two layers of electrically conductive material; a means to provide electrical connection from the first layer of said two layers of electrically conductive material to a second pole of said two pole direct current power source; and a means to hold said device together in a portable case.

2. The alarm of claim 1 where said alarm is a light and sound emitting device.

3. A hypodermic syringe needle detection alarm device for use in searching inside cavities for hypodermic syringe needles comprising a direct current power source with a positive pole and a negative pole; a means to provide electrical connection from said positive pole of said power source to a layer of an electrically conductive material, said layer being the layer of conductive material which rests closest to the portable case such that it is the innermost of two conductive layers; a second electrically conductive layer of material, said second conductive layer being the conductive layer which rests closest to the external environment such that it is the outermost of two conductive layers; said two conductive layers having situated between them an electrically non-conductive layer of material; said outermost conductive layer having a means to provide electrical connection to a relay; said relay having a means to provide electrical connection to the negative pole of said power source; such that when the above circuit is completed by the insertion of a hypodermic syringe needle of electrically conductive construction so that said needle makes electrical contact between said innermost conductive layer and said outermost conductive layer said relay is closed; said relay having a means to provide electrical connection to one terminal of a two terminal lamp; said lamp having a means to provide electrical connection to negative pole of said power source from one said terminal of said lamp; said relay having a means to provide electrical connection to the positive pole of said power source so that when said relay is closed the lamp is lit; and a portable case.

4. The means to provide electrical connection of claim 3 where said means to provide electrical connection is metal wire.

5. The power source of claim 3 where said power source is dry cell batteries.

6. The layer of electrically conductive material of claim 3 where said layer of electrically conductive material is aluminum foil.

7. The layer of electrically non-conductive material of claim 3 where said non-conductive material is plastic stretch wrap.

8. The relay of claim 3 where said relay is a double pole single throw relay.

9. The lamp of claim 3 where said lamp is a light emitting diode.

10. The lamp of claim 3 where said lamp is an incandescent lamp.

11. The portable case of claim 3 where said portable case is a plastic portable case.

12. The portable case of claim 3 where said portable case is an aluminum case.

13. An alarm device for use in searching for hypodermic syringe needles comprising a unit which is portable, handheld, dry cell battery powered, and emits an alarm when the device is pierced by a hypodermic syringe needle; comprising a detection circuit, an alarm circuit, a two pole power source and a portable case; said detection circuit comprising external detection layers such that said external detection layers are situated on the outside of said case and a means to conduct electricity through the electrically active parts of said device, more particularly described as comprising a base layer of material which is bonded to the case, said base layer being an insulator and being covered by a second layer of electrically conductive material and having a means to provide electrical connection to said second layer from one pole of said power source; said second layer being covered by a third layer of electrically non-conducting material sufficiently permeable to permit the passage through it of a hypodermic syringe needle; said third layer being covered by a fourth layer comprising an electrically conductive material which is sufficiently permeable to permit the passage through it of a hypodermic syringe needle while at the same time maintaining electrical contact with said hypodermic syringe needle which has passed through said fourth layer sufficiently to also pass through said third layer and make electrical contact with said second layer; a means to provide electrical connection from said fourth layer to one pole of a two pole electromagnet; a fifth layer of material sufficiently permeable to permit the passage through it of a hypodermic syringe needle covering said fourth layer; said electromagnet is connected to a switch in such a manner that when said electromagnet is supplied with power said electromagnet moves moving poles of said switch; said electromagnet having a means to provide electrical connection from the second pole of said electromagnet to the second pole of said power source; such that said device makes a normally open circuit where the one and only point of opening lies in the space between the two said layers of electrically conductive material; said switch comprising four electrically conductive terminals and two moving poles arranged in such a manner that one terminal of said switch is attached to one said moving pole and a second such terminal is attached to the second said moving pole in such a manner that such attachment provides a means of electrical connection between said terminals and said moving poles, said third and fourth terminals are arranged in such a manner that said third terminal will make electrical contact with one of the said moving poles and that said fourth terminal will make electrical contact with the other moving pole when and only when said moving poles are caused to move by said electromagnet and where in the absence of electrical power to said electromagnet there is no electric current passing through said terminals of said switch but when the electromagnet is activated by electricity said moving poles move to make electrical contact between two sets of two terminals on said switch; said circuit which drives the electromagnet being the detection circuit; the alarm circuit comprising a warning emit circuit and a warning lock circuit, the warning emit circuit comprising a means to provide electrical connection from one pole of said two pole power source to one terminal of said electromagnetically driven switch, said terminal being electrically connected to one of said moving poles; said one moving pole being separated by air space from a third terminal on said switch so situated that when the abovementioned moving pole moves in response to the electromagnet being driven said moving pole achieves electrical contact with said third terminal; a means to provide electrical connection from said third terminal of said switch to one pole of a two pole lamp; a means to provide electrical connection from the second pole of said lamp to the second pole of said power source; such that this warning emit circuit is normally open with a point of opening being the airspace between the aforesaid moving pole and the aforesaid third terminal of said switch and being so situated that when said electromagnet drives said switch said moving pole and said third terminal electrically connect and the circuit is closed and said lamp is lit; the warning lock circuit comprising a means to provide electrical connection from one pole of said two pole power source to the second said terminal on said switch which is electrically connected to the second said moving pole; a means to provide electrical connection from the said fourth terminal of said switch to one said terminal of said electromagnet; a means to provide electrical connection from the second said terminal of said electromagnet to the second said pole of said power source; said warning lock circuit being normally open at one and only one point which is the airspace between said second moving pole and said fourth terminal of said switch, said pole and said fourth terminal making electrical contact only when said electromagnet is driven by electricity, and once said electromagnet is driven said warning lock will maintain electrical power to said electromagnet; said portable case comprising a portable unit which holds said device in such a manner that said detection layers will be exposed for piercing by a hypodermic syringe needle and where said lamp will be visible when the detection layers are in use.

14. The base layer of claim 13 where said base layer is a cork base layer.

15. The electrically conductive material of claim 13 where said electrically conductive material is aluminum foil.

16. The electrically non-conductive material of claim 13 where said material is plastic stretch wrap.

17. The electromagnet and switch of claim 13 where said electromagnet and switch are a double pole single throw relay.

18. The power source of claim 13 where said power source is dry cell batteries.

19. The external detection layers of claim 13 where said layers are removable and replaceable.

20. The detection circuit of claim 13 where said detection circuit includes an on/off switch between one pole of the power source and the rest of the circuit.

* * * * *